Figure 1:
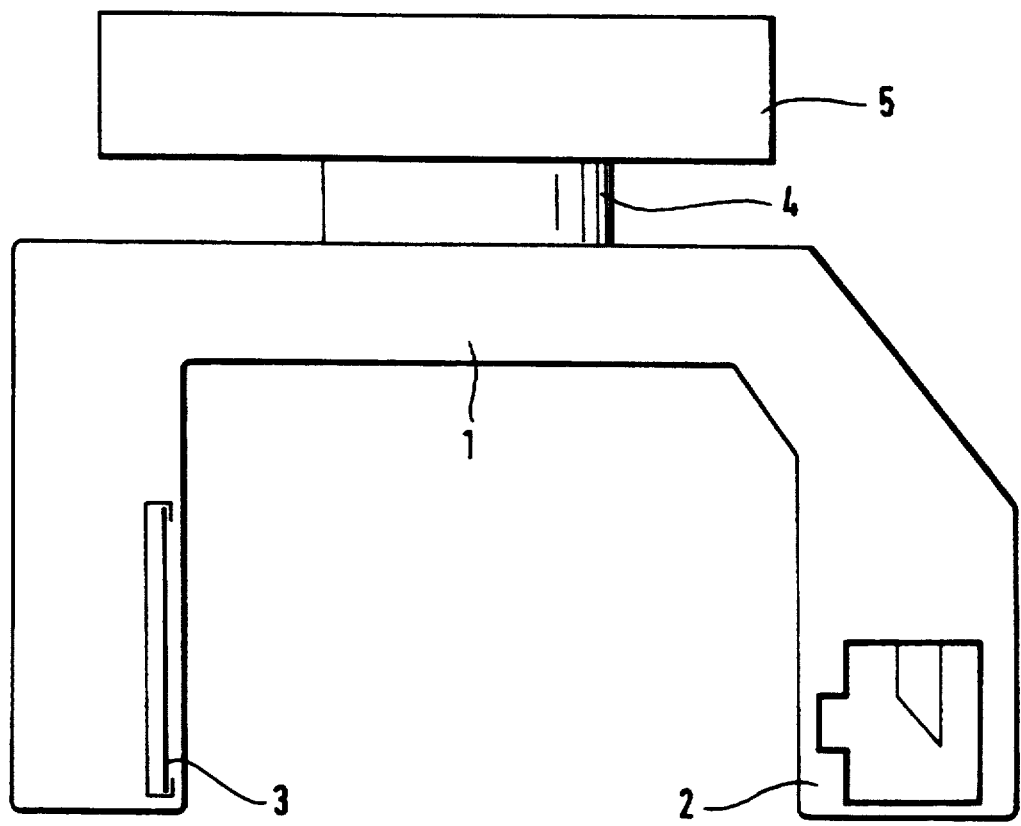

United States Patent [19]

Kanerva et al.

[11] Patent Number: 5,371,775
[45] Date of Patent: Dec. 6, 1994

[54] METHOD OF USING A PANORAMIC X-RAY PHOTOGRAPHY APPARATUS FOR TOMOGRAPHY

[75] Inventors: Heikki Kanerva, Turku; Matti Wahlström, Helsinki, both of Finland

[73] Assignee: Orion-yhtyma Oy, Helsinki, Finland

[21] Appl. No.: 64,254

[22] Filed: May 20, 1993

[30] Foreign Application Priority Data

May 22, 1992 [FI] Finland .................................. 922361

[51] Int. Cl.$^5$ .............................................. A61B 6/14
[52] U.S. Cl. ........................................ 378/38; 378/39; 378/168
[58] Field of Search .................... 378/38, 39, 40, 167, 378/168, 193

[56] References Cited

U.S. PATENT DOCUMENTS

| | | |
|---|---|---|
| 4,039,837 | 8/1977 | Ohta et al. . |
| 4,241,254 | 12/1980 | Välilä . |
| 4,263,513 | 4/1981 | Palluet . |
| 4,264,820 | 4/1981 | Hotta . |
| 4,661,967 | 4/1987 | Nishikawa ............................ 378/39 |
| 4,852,134 | 7/1989 | Kinanen et al. ...................... 378/38 |
| 4,955,042 | 9/1990 | Nishikawa ............................ 378/39 |
| 4,985,907 | 1/1991 | Moteni ............................ 378/38 X |
| 5,012,501 | 4/1991 | Palonen et al. ...................... 378/38 |

FOREIGN PATENT DOCUMENTS

| | | | |
|---|---|---|---|
| 0035307 | 9/1981 | European Pat. Off. | .............. 378/39 |
| 340349 | 11/1989 | European Pat. Off. . | |
| 3441012 | 5/1985 | Germany . | |
| WO79/00065 | 2/1979 | WIPO . | |

*Primary Examiner*—David P. Porta
*Attorney, Agent, or Firm*—Marshall, O'Toole, Gerstein, Murray & Borun

[57] ABSTRACT

The invention relates to a panoramic X-ray photography apparatus having a rotatably mounted supporting arm (1) which has at one end an X-ray source (2) and at the opposite end an image receptor (3), in which case the object is placed between the X-ray source (2) and the image receptor (3) and the imaging is carried out by rotating the supporting arm. The idea of the invention is that a simple panoramic X-ray photography apparatus can also be used for tomography, since the object to be imaged, i.e. the denture, contains mainly vertical surfaces and a horizontal oscillating movement suffices for blurring them. An additional idea is that by moving the bearing shaft (4) of the supporting arm along a circle arc portion during blurring, the fulcrum can be shifted to outside the bearing shaft, thus eliminating certain limitations imposed by the mechanics of a conventional X-ray photography apparatus with respect to the area to be imaged and the location of the supporting arm.

4 Claims, 3 Drawing Sheets

METHOD OF USING A PANORAMIC X-RAY PHOTOGRAPHY APPARATUS FOR TOMOGRAPHY

The present invention relates to a panoramic X-ray photography apparatus having a rotatably mounted supporting arm, which has at one end an X-ray source and at the opposite end an image receptor, in which case the object to be imaged is placed between the X-ray source and the image receptor and the imaging is carried out by rotating the supporting arm, the bearing shaft of the supporting arm being suspended so that the shaft can be moved in different directions during rotation.

Such panoramic X-ray photography apparatuses are normally used for imaging the denture or jaws of a patient. In normal imaging the entire dental arch is imaged using a narrow cone of rays, in one continuous scan, the image receptor being moved in the opposite direction at a velocity which corresponds, in the area of the image receptor, the projection velocity of the layer of which a sharp image is desired.

For example, from patent U.S. Pat. No. 4,852,134 it is known to combine in the same apparatus the facilities for both panoramic imaging and tomography. By tomography, i.e. layered imaging, is meant a method in which the imaging is carried out in a central projection by using a field of rays covering the object being imaged, the field of rays moving around a point or axis in the object being imaged, the image receptor remaining stationary in relation to the field of rays, whereupon a sharply imaged layer is formed at the point or axis, while the areas outside the layer are blurred, depending on the extent of the movement, among other things.

In an apparatus according to the said US patent, tomography is effected by a combined vertical and transverse oscillating movement. The structure of the apparatus deviates from that of a conventional panoramic apparatus as regards the C-arch system, which makes a vertical oscillating movement possible.

There are also known separate apparatuses intended specifically for tomography, but these are considerably more expensive than panoramic X-ray photography apparatuses.

A conventional panoramic apparatus has the disadvantage that in it the dental arch is imaged only in a substantially perpendicular projection, in which depth information in the direction of the imaging ray will remain deficient. As disclosed in the said US patent, tomography can be used for transverse imaging of the dental arch.

The invention is based on the observation that transverse tomography can be performed sufficiently, well and simply by making use of part of the rotational movement of a conventional panoramic apparatus. A denture mainly contains vertical boundary surfaces, and their good blurring can be effected by means of a movement transverse to the boundary surfaces.

One problem in the use of a panoramic X-ray photography apparatus for tomography and for examinations more extensive than merely the imaging of the dental arch consists of mechanical limitations. Often the rotation shaft is tubular and the support for the patient's head extends downwards through this tube, which of course limits the locating of the supporting arm in relation to the patient.

The object of the present invention is now to eliminate these problems and to implement a conventional panoramic X-ray photography apparatus in such a manner that it can, without expensive structural means, be used for tomography, and that, furthermore, the limitations imposed by the mechanics are eliminated at least in part.

To achieve this object the invention is characterized in what is stated in accompanying claim 1.

One idea of the invention is thus that a panoramic X-ray photography apparatus can well be used for cross-sectional tomography in the area of the dental arch, where the need for its use is greatest, since the question is mainly of the blurring of vertical surfaces. Also the buccal and lingual surfaces of the jaw are vertical. Another substantial improvement is also that, owing to the invention, the apparent fulcrum of the imaging ray can be shafted to outside the bearing shaft of the supporting arm itself.

In normal panoramic imaging the rotation axis is almost without exception moved during the imaging. A linear movement is used either in the direction of the axis of symmetry (Y-movement) or a transverse movement (X-movement), or the path of movement of the axis mimics, for example, the shape of the dental pattern. It is also essential that the image receptor, i.e. the film, is moved in synchronization with the scanning beam. In tomography, on the other hand, the film remains stationary in relation to the beam of X-rays, and in conventional tomography carried out using a panoramic apparatus also the shaft of the arm remains stationary during the reciprocal rotational movement. The present invention now provides a change with respect to this.

Figure 2:
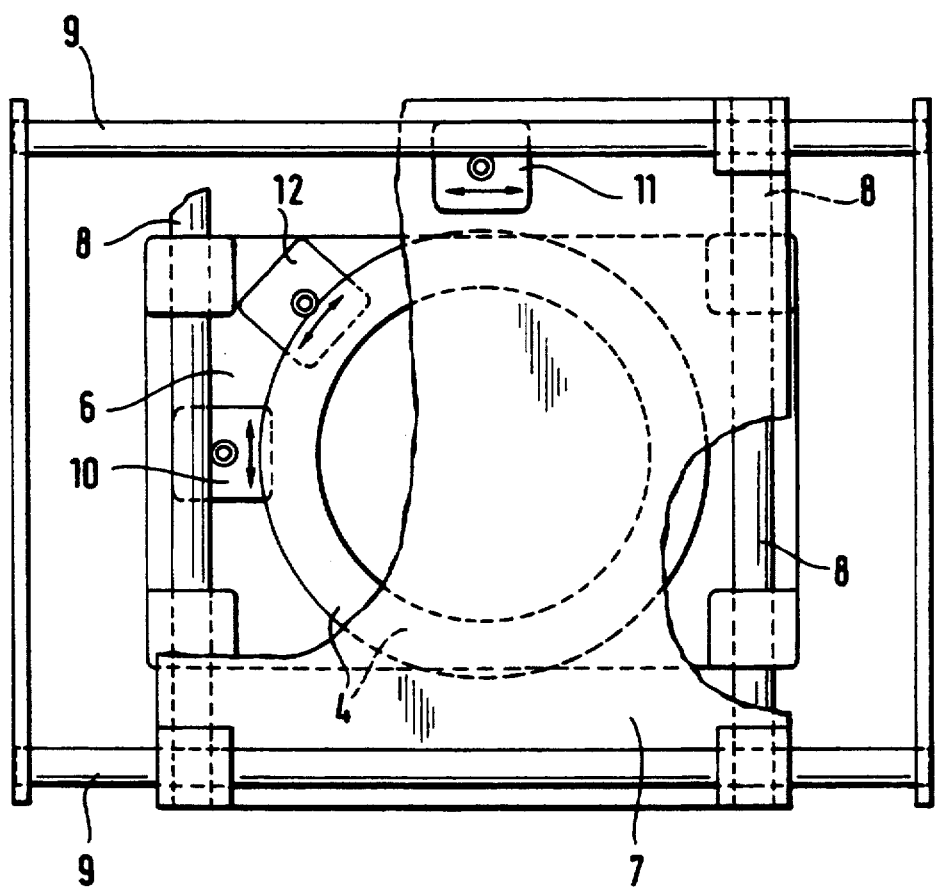
Figure 3:
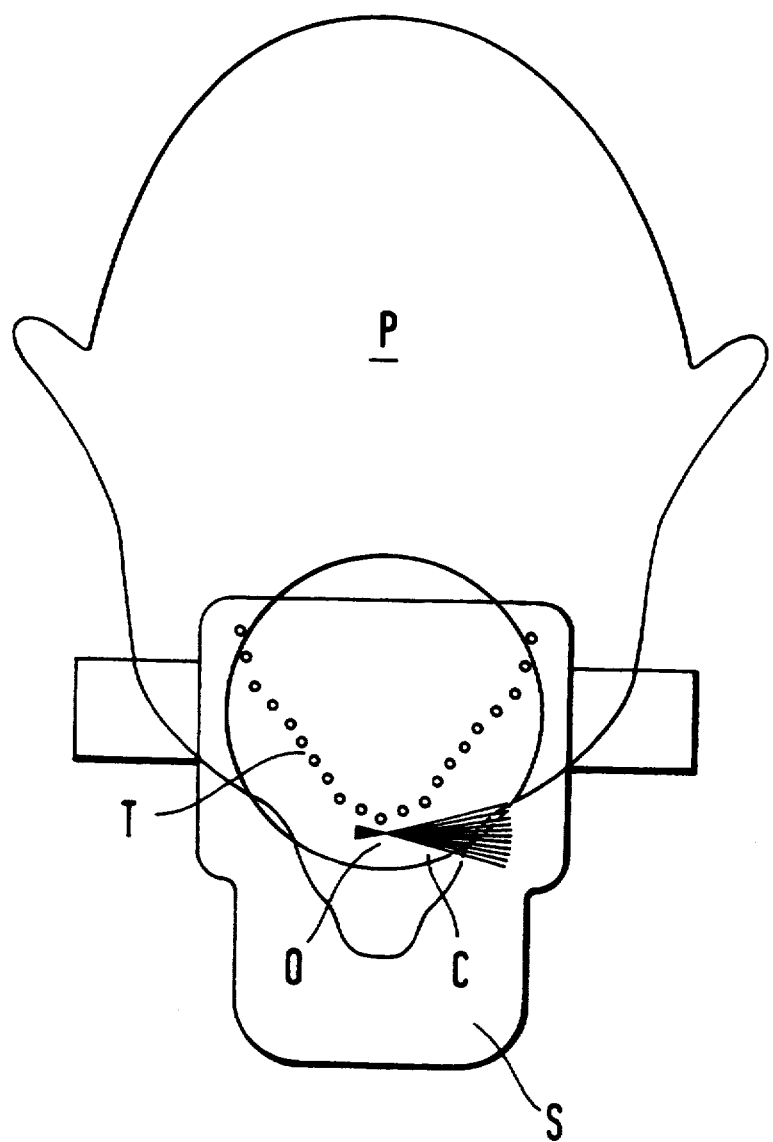

The invention and its other features and advantages are described below in greater detail, in the form of an example and with reference to the accompanying drawings, in which FIG. 1 depicts schematically a side view of a conventional panoramic X-ray photography apparatus, FIG. 2 depicts the suspension of the supporting arm of the panoramic X-ray photography apparatus, and FIG. 3 depicts a top view of the patient's head and the cone of rays.

In FIG. 1, reference numeral 1 indicates the so-called supporting arm of a panoramic X-ray photography apparatus, the arm having at one end an X-ray source 2 and at the opposite end an X-ray film 3 serving as the image receptor. As is well known, the patient's head is placed, with the help of certain head-supporting means, between the X-ray source 2 and the film 3, and the imaging is carried out by rotating the supporting arm about its bearing shaft 4. Normally the bearing shaft is further suspended from a mechanism 5 which allows the movement of the rotation shaft 4 during rotation.

FIG. 2 shows schematically a suspension mechanism (which corresponds to part 5 in FIG. 1) which enables the rotation shaft 4 to be moved during imaging, in both the X-direction and the Y-direction. The tubular rotation shaft 4 is mounted to a plate 6, which is mounted so as to move along two parallel shafts 8. These shafts 8 in turn are attached to another plate 7, which can be moved along two shafts 9, which are perpendicular to the shafts 8. The movement along the shafts 8 is produced by a step motor 10, and the movement along the shafts 9 respectively by a step motor 11. The shaft 4 rotatably mounted to the plate 6 can be rotated by means of a step motor 12. Thus an arrangement is obtained in which the center point of the shaft 4 can be moved, controlled at will, in the x-y plane during the rotation of the shaft.

When the apparatus is used in accordance with the invention for tomography, the supporting arm 1 is oscillated with only a small amplitude around a certain position. In FIG. 3, the small circles T depict the various points in the dental arch of the patient P which are blurred one by one, the location of the supporting arm being changed betweentimes. In the figure, letter S indicates the patient's head rest and the circle indicates the location area which is delimited by the mechanics of the X-ray apparatus.

The limitations imposed by the mechanics can be partly eliminated or they can be reduced according to the invention by moving the bearing shaft 4 itself during the blurring. More precisely, the shaft 4 is moved by means of the plates 6, 7 and the motors 10, 11 during the blurring along the circle arc portion C, whereby the apparent fulcrum 0 of the arm or the ray can be shifted to outside the bearing shaft 4 itself. However, both the fulcrum and the bearing shaft are located in the central plane of the cone of rays. The circle arc C is adjusted so that its center point will be within the area to be imaged.

The invention described above will not require mechanical changes in a panoramic X-ray apparatus; it can be effected by the control of the motors. One of the advantages gained is that the dimensions of the x-y movements, intended merely for locating purposes, may be smaller than conventional, which is a clear advantage in terms of cost in a panoramic X-ray apparatus.

We claim:

1. A method of using a panoramic X-ray photography apparatus for tomography, said apparatus comprising: a supporting arm (1) rotatably mounted on a rotatable bearing shaft (4), an X-ray source (2) emitting a limited cone of X-rays disposed at one end of said arm, and an image receptor (3) disposed at an opposite end of said arm, said bearing shaft (4) being suspended such that said shaft is movable in different directions during rotation, said method comprising the steps of:

(a) disposing an object to be imaged between said X-ray source (2) and said image receptor (3);

(b) rotating said supporting arm (1) to a limited extent about said bearing shaft (4) without said image receptor (3) being moved with respect to said X-ray source (2); and (c) moving said bearing shaft (4) along a limited circle arc (C) such that an apparent axis of rotation (O) of said image receptor (3) is shifted to outside the bearing shaft (4).

2. The method of claim 1, wherein said bearing shaft (4) is suspended from two carriages (6, 7) that move perpendicularly with respect to each other.

3. The method of claim 1, wherein the position of said limited circle arc is such that said apparent axis of rotation is disposed within an area to be images.

4. The method of claim 3, wherein said bearing shaft (4) is suspended from two carriages (6, 7) that move perpendicularly with respect to each other.

* * * * *